United States Patent [19]

Stewart

[11] Patent Number: 5,387,450
[45] Date of Patent: Feb. 7, 1995

[54] TEMPERATURE-ACTIVATED ADHESIVE ASSEMBLIES

[75] Inventor: Ray F. Stewart, Redwood City, Calif.

[73] Assignee: Landec Corporation, Menlo Park, Calif.

[21] Appl. No.: 842,873

[22] Filed: Feb. 27, 1992

Related U.S. Application Data

[63] Continuation-in-part of Ser. No. 497,940, Mar. 23, 1990, abandoned, which is a continuation-in-part of Ser. No. 350,723, May 11, 1989, Pat. No. 5,156,911.

[51] Int. Cl.$^6$ ................................................ C09J 7/02
[52] U.S. Cl. ...................................... 428/40; 428/261; 428/339; 428/355
[58] Field of Search .................. 428/343, 355, 349, 40, 428/261, 339

[56] References Cited

U.S. PATENT DOCUMENTS

| | | | |
|---|---|---|---|
| 2,462,029 | 2/1949 | Perry | 428/346 |
| 2,484,045 | 10/1949 | Morgan | 602/42 |
| 3,059,764 | 10/1962 | Tomita et al. | 428/346 |
| 3,284,423 | 11/1966 | Knapp | 526/218.1 |
| 3,299,010 | 1/1967 | Samour | 428/355 |
| 3,342,623 | 9/1967 | Dulmage et al. | 430/271 |
| 3,508,944 | 4/1970 | Henderson et al. | 428/346 |
| 3,535,295 | 10/1970 | Davis et al. | 525/193 |
| 3,612,053 | 10/1971 | Pratt | 128/283 |
| 3,635,754 | 1/1972 | Beede | 428/349 |
| 3,645,835 | 2/1972 | Hodgson | 428/195 |
| 3,690,937 | 9/1972 | Guse et al. | 427/208.4 |
| 3,763,858 | 10/1973 | Buese | 128/156 |
| 3,838,079 | 9/1974 | Kosaka et al. | 524/271 |
| 3,896,789 | 7/1975 | Trancik | 604/307 |
| 4,066,600 | 1/1978 | Pletcher | 428/355 |
| 4,139,675 | 2/1979 | Nagai et al. | 428/349 |
| 4,199,646 | 4/1980 | Hori et al. | 428/344 |
| 4,323,557 | 4/1982 | Rosso et al. | 424/28 |
| 4,356,222 | 10/1982 | Harakawa et al. | 428/78 |
| 4,393,116 | 7/1983 | Taylor | 428/343 |
| 4,404,243 | 9/1983 | Terpay | 428/354 |
| 4,460,371 | 7/1984 | Abber | 604/897 |
| 4,551,388 | 11/1985 | Schlademan | 428/355 |
| 4,564,010 | 1/1986 | Coughlan et al. | 128/156 |
| 4,588,762 | 5/1986 | Mruk | 428/355 |
| 4,610,908 | 9/1986 | Reylek et al. | 428/141 |
| 4,619,851 | 10/1986 | Sasaki et al. | 428/40 |
| 4,633,276 | 12/1986 | Shibata et al. | 346/200 |
| 4,675,009 | 6/1987 | Hymes et al. | 604/304 |
| 4,693,776 | 9/1987 | Krampe et al. | 156/327 |
| 4,738,472 | 4/1988 | Shibata | 283/101 |
| 4,769,285 | 9/1988 | Rasmussen | 423/355 |
| 4,784,653 | 11/1988 | Bolton et al. | 604/307 |
| 4,789,285 | 12/1988 | Fischer | 411/32 |
| 4,830,855 | 5/1989 | Stewart | 424/448 |
| 4,880,683 | 11/1989 | Stow | 428/355 |
| 4,904,243 | 2/1990 | Bruera | 604/183 |
| 4,925,908 | 5/1990 | Bernard et al. | 526/320 |
| 5,156,911 | 5/1989 | Stewart | 428/355 |

FOREIGN PATENT DOCUMENTS

| | | |
|---|---|---|
| 062682 | 10/1980 | European Pat. Off. |
| 0083499 | 7/1983 | European Pat. Off. |
| 63-202682 | 8/1988 | Japan |
| WO8403837 | 10/1984 | WIPO |
| 9013420 | 11/1990 | WIPO |
| WO9114461 | 3/1991 | WIPO |
| WO9114462 | 3/1991 | WIPO |

OTHER PUBLICATIONS

Makromol. Chem. Rapid Commun. 7, 33–36 (1986) (Hackbarth and Ritter).

(List continued on next page.)

*Primary Examiner*—Jenna L. Davis
*Attorney, Agent, or Firm*—Jeffrey G. Sheldon

[57] ABSTRACT

Temperature-activated adhesive compositions formulated with crystallizable polymers are provided. The compositions, which display a rapid transition from the tacky to the nontacky state, and/or from the nontacky to the tacky state, are useful in medical applications, where adhesion of a substrate to the skin is desired, as well as in a variety of nonmedical applications. Temperature-activated adhesive assemblies such as tapes, labels, and the like for use in a number of contexts are provided which assemblies have a moisture vapor transmission rate which is compatible with human skin, e.g., above 500 g/m$^2$/day at 37° C. and a 100% to 10% relative humidity difference.

29 Claims, No Drawings

OTHER PUBLICATIONS

S. C. Temin, *Encyclopedia of Polymer Science and Engineering*, vol. 13 (New York, John Wiley & Son, 1988), pp. 345–368.

Handbook of Pressure-Sensitive Adhesive Technology, Ed. Don Satas (New York, Van Nostrand Reinhold Co., Inc., 1982), pp. 50–77, 299–330, 331–425, and 575–585.

A. H. Landrock, *Adhesives Technology Handbook*, (Park Ridge, N.J., Noyer Publications, 1985).

J. Poly. Sci. Physics Ed. 18:2197 (1980).

Ed Cagle, Handbook of Adhesive Bonding (McGraw-Hill Book Co., 1973) ch. 8, pp. 1–17.

Miyauchi, J. Polymer Sci.: Macromolecular Review 8: 117–252 (1974).

J. Poly. Sci. 7:3053 (1969).

J. Poly. Sci. 10:3347 (1972).

J. Poly. Sci. 10:1657 (1972).

J. Poly. Sci. 9:3367 (1971).

J. Poly. Sci. 17:991 (1985).

J. Poly Sci. 60:19 (1962).

J. Poly. Sci. 9:3349 (1971).

J. Poly. Sci. 9:1835 (1971).

J. Poly Sci. Chemistry Ed. 19:1871–1873 (1981).

J. Am. Chem. Soc. 76:6280 (1954).

Macromolecules 13:12 (1980).

Macromolecules 13:15 (1980).

J. Am. Chem. Soc. 75:3326 (1953).

Macromolecules 18:2141.

Macromolecules 12:94 (1979).

J. Poly. Sci. U.S.S.R. 21:241.

Macromolecules 19:611 (1986).

TEMPERATURE-ACTIVATED ADHESIVE ASSEMBLIES

CROSS-REFERENCE TO RELATED APPLICATIONS

This application is a continuation-in-part of our earlier filed U.S. application Ser. No. 07/497,940, filed Mar. 23, 1990, now abandoned, which is a continuation-in-part of U.S. patent application Ser. No. 07/350,723, filed May 11, 1989, now U.S. Pat. No. 5,156,911, both of which applications are incorporated herein by reference and to which applications we claim priority under 35 USC §120.

TECHNICAL FIELD

The present invention relates to adhesive compositions and assemblies, and more particularly concerns temperature-activated adhesive assemblies such as tapes and bandages which have a moisture vapor transmission rate compatible with human skin.

BACKGROUND

Pressure-sensitive adhesives (PSA) are well known and are used for a variety of industrial, consumer and medical applications. Pressure-sensitive adhesives are characterized as being normally tacky and exhibiting instant tack when applied to a substrate. A variety of polymers have been used to manufacture PSA, for example, acrylic and methacrylic ester homo- or copolymers, butyl rubber-based systems, silicones, urethanes, vinyl esters and amides, olefin copolymer materials, natural or synthetic rubbers, and the like.

Flexible polymeric film materials are also known such as described in European Patent Applications Nos. 0107915 and 0147119 and PCT/GB91/00496 all of which being incorporated herein by reference to disclose materials with particular moisture vapor transmission rates which might be used as backing materials in connection with the present invention. Film materials which have moisture vapor transmission rates generally compatible with human skin are most preferred.

S. C. Temin, in the *Encyclopedia of Polymer Science and Engineering*, vol. 13 (New York: John Wiley & Sons, 1988), at pp. 345-368, and the *Handbook of Pressure-sensitive Adhesive Technology*, ed. Donates Satas (New York: Van Nostrand Reinhold Co., Inc., 1982), both provide a comprehensive overview of medical and other adhesives. A. H. Landrock, *Adhesives Technology Handbook* (Park Ridge, N.J.: Noyes Publications, 1985), pp. 154-156, and T. Flanagan, "Hot-melt Adhesives" in the *Handbook of Adhesive Bonding*, ed. C. V. Cagle (New York: McGraw-Hill, 1982), at pp. 8-1 to 8-17, describe hot-melt adhesives, i.e., adhesives which are applied to a substrate as a melt and which solidify and bond upon cooling. In contrast to the adhesive compositions of the present invention, hot-melt adhesives involve flowable polymers and do not allow for reversible adhesion.

U.S. Pat. No. 3,635,754 to Beede describes a temporary pressure-sensitive polyolefin-based adhesive product which is activated by heating at least 15° C. above its melting point, and which, after cooling, remains tacky for an extended period of time.

U.S. Pat. No. 3,284,423 to Knapp describes a pressure-sensitive, cross-linked adhesive copolymer which is claimed to be storage stable in solution but readily cured when coated and heated. The copolymer consists of acrylic acid esters, lower alkyl acrylates (1-8 carbons, preferably 1-4 carbons), acrylic acid and glycidyl acrylate or methacrylate.

U.S. Pat. No. 3,535,195 to Davis et al. describes a pressure-sensitive, amine-containing adhesive which is stated to exhibit good tack yet be easily removable from a substrate.

U.S. Pat. No. 3,690,937 to Guse et al. relates to pressure-sensitive adhesives formulated from di-alkyl fumarates.

U.S. Pat. No. 3,838,079 to Kosaka et al. describes copolymer resins prepared from alkyl acrylates (1-20C) and maleic anhydride.

U.S. Pat. No. 3,299,010 to Samour describes a variety of adhesive compositions, some of which contain C-12 to C-24 residues. The patent teaches that the higher alkyl residues must be branched in order to avoid crystallinity. Some of the compositions contain acrylamido or other polar groups, and claims of adhesion to moist skin are made.

U.K. Patent No. 870,022, inventors Dahlquist and Zenk, teaches the use of a copolymer of octadecyl acrylate, acrylonitrile, ethyl acrylate, and acrylic acid as a low adhesion backsize on a pressure-sensitive adhesive tape.

PCT Publication No. WO84/03837 teaches the use of copolymers which contain a polyalkylene oxide monomer in addition to acrylate. The polyoxyalkylene moiety is stated to impart hydrophilic behavior to the adhesive composition, thus facilitating adhesion to moist skin.

European Patent Application Publication No. 062682 describes the use of the monomer dodecyl methacrylate in a copolymer employed as an adhesive carrier for nitroglycerine. Small amounts of other comonomers (acrylic acid and short chain acrylates) are added to the reaction mixture to improve the properties of the copolymer.

The following references relate to side-chain crystallizable polymers: *J. Polymer Sci.: Macromoleculer Review* 8:117 (1974) and J. Polymer Sci.: *Polymer Chemistry Edition* 19:1871-1873 (1981).

A PCT publication, WO91/14462, published October 3, 1991 refers to medical devices comprised of a substrate with a particular moisture vapor transmission rate with an adhesive thereon which is tacky at skin temperature but less tacky or not tacky at room temperature. A similar medical adhesive device is disclosed in WO91/14461. The disclosure of both of these PCT publications is incorporated herein by reference to the extent they disclose such devices including particular backing layers, adhesives and methods of use and manufacture.

SUMMARY OF THE INVENTION

The invention comprises a substrate with an adhesive thereon. The substrate is preferably in the form of a flexible sheet or tape which may be a polymer or woven material suitable for forming a bandage. The adhesive is comprised of a crystallizable polymer which is not tacky at room temperature but undergoes a first order phase transition at a temperature just below skin temperature and becomes and remains highly tacky on the skin. The phase transition is reversible so that upon cooling the polymer reverts to its non-tacky state. The substrate and polymer are combined in an assembly which has a moisture vapor transition rate which is skin compatible.

An important aspect of the invention is to provide a medical bandage or tape having a moisture vapor transmission rate compatible with skin comprised of a flexible backing and a temperature-activated adhesive comprised of a crystallizable polymer tacky at skin temperature and non-tacky at room temperature.

An object is to provide such a bandage or tape wherein the backing has a moisture vapor transmission rate of more than 100 g/m$^2$/day, more preferably more than 500 g/m$^2$/day.

It is also an object of the invention to provide a medical adhesive assembly, specifically, which can be removed from the skin with less force, pulling and trauma than conventional adhesive tapes and bodies necessitate.

It is another object of the invention to provide a temperature-activated, pre-positionable medical adhesive assembly which is substantially nontacky at room temperature, becomes tacky upon application to skin, and retains adhesivity indefinitely.

It is still another object of the invention to provide a medical adhesive assembly which is aggressively tacky at skin temperature, and which rapidly loses adhesion upon cooling.

It is a further object of the invention to combine the advantages and characteristics of the latter two embodiments, in providing a pre-positionable medical adhesive assembly which is substantially nontacky at room temperature, becomes aggressively tacky upon contact with the skin, and loses adhesivity upon cooling.

Still a further object of the invention is to provide temperature-activated adhesive assemblies useful as labels.

Yet an additional object of the invention is to provide "warm-activated" adhesive assemblies formulated with an adhesive composition that is normally nontacky but which may be rendered tacky when warmed to a temperature just slightly above room temperature.

It is still a further object of the invention to provide methods of making and using the aforementioned adhesive assemblies.

Additional objects, advantages and novel features of the invention will be set forth in part in the description which follows, and in part will become apparent to those skilled in the art on examination of the following, or may be learned by practice of the invention.

The adhesive comprises a polymeric composition containing a polymer having a first-order melting transition which occurs over a melting range less than about 15 centigrade degrees, the polymer being present in the composition in an amount effective to render the adhesive substantially nontacky at temperatures below the melting range and tacky at temperatures within or above the melting range. A sharp transition from tacky to nontacky, or from nontacky to tacky, can be achieved by preparing a polymer composition which has a high level of crystallinity at a low temperature (e.g., room temperature of about 20° C.) but becomes highly amorphous and tacky after a phase transition at a slightly higher temperature (e.g., skin temperature of about 37° C.).

The invention is also directed to temperature-activated adhesive assemblies for use in medical applications, i.e., adhesive assemblies which make use of the aforementioned adhesive and are particularly useful for adherence to the skin and as such has a skin compatible moisture transmission rate of more than 100 g/m$^2$/day, more preferably more than 500 g/m$^2$/day at 37° C. and 10% relative humidity.

The first of these medical adhesive assemblies is a temperature-activated, "pre-positionable" medical adhesive assembly comprising a body member having a surface coated with an adhesive composition that is substantially nontacky at room temperature and tacky at skin temperature. By "pre-positionable" is meant an assembly which can be positioned and maneuvered about, at room temperature, or any other temperature below its application temperature, without unwanted adhesion until it contacts and is warmed by skin or some other substrate which causes the adhesive component to experience an elevation of its temperature above the transition point such that the adhesive component becomes aggressively tacky and adheres to the skin or other substrate.

The second medical adhesive assembly comprises a body member having a surface coated with an adhesive composition which, while tacky at, or slightly below skin temperature, loses adhesivity upon cooling 5 to 15 degrees Celsius below that temperature.

The third medical adhesive assembly combines the features of both of the aforementioned embodiments in that it is both pre-positionable (i.e., substantially nontacky at room temperature), aggressively tacky at skin temperature, and capable of losing adhesivity upon cooling.

These adhesive assemblies may be adhesive tapes in which a flexible backing is coated with a selected polymer, or they may comprise casts, splints or other immobilization devices which have been similarly coated. Thus, some medical products contemplated by the present invention have solid, inflexible backings. Where the composition provides temperature-reversible adhesion, strong bonding will be provided during use, i.e., between the immobilization device and the skin, but after use, upon cooling, the adhesive becomes substantially less adhesive, allowing easy-removal of the immobilization device.

Nonmedical adhesive assemblies are also within the scope of the present invention, and include temperature-sensitive labels or tape which stick aggressively to a substrate during the desired period of use but which are readily removable upon chilling; and warm-activated adhesive assemblies which are normally nontacky but which become tacky when warmed to a temperature slightly above room temperature.

Any of the adhesive assemblies which have flexible backings and are for medical use preferably have a moisture vapor transition rate of more than 100 g/m$^2$/day and more preferably more than 500 g/m$^2$/day.

DETAILED DESCRIPTION OF THE INVENTION

The invention is thus directed to temperature-activated adhesive assemblies useful in a variety of medical and nonmedical applications. All of the temperature-activated adhesive assemblies of the invention make use of a polymeric composition comprising a polymer which has a first-order melting transition between about 5° C. and about 50° C., and wherein that transition occurs over a melting range of less than about 15 centigrade degrees, more preferably over a range of less than about 10 centigrade degrees. Such a narrow range for the melting transition ensures that the transition from the tacky state to the substantially nontacky state (and/or vice versa) will be quite rapid. In all of the presently disclosed assemblies, in addition, the aforementioned polymer is present in an amount effective to render the adhesive composition substantially nontacky at temperature below the melting range and tacky at temperatures within or above the melting range. These adhesive assemblies include the medical adhesive assemblies disclosed in parent applications Ser. Nos. 07/350,723 and 07/497,940, as well as the additional types of adhesive assemblies described and claimed herein.

The ideal performance characteristics of an adhesive intended for use on human skin, specifically, present difficult and conflicting technical requirements. The ideal medical adhesive should, first of all, be nonirritating yet bond quickly to skin at the intended site of use. At the same time, clearly, it should not stick to other objects until it is actually applied to the target site. The adhesive should maintain its bond for as long a period of time as necessary and be resistant to inadvertent removal. Furthermore, the adhesive should not be weakened or destroyed by exposure to moisture or high humidity. In addition, in order to provide protection to a wound or to maintain the integrity of placement of an electrode or other device the adhesive should resist skin movement and be able to transfer a mechanical load from the adhesive backing to the skin. Lastly, the assembly should be designed so that the moisture vapor transmission rate is skin compatible. Thus, air and water vapor can be exchanged across the assembly but bacteria and liquid moisture are kept out.

Assemblies of the invention are particularly useful in medical applications (i.e., for adhering to the skin), when they meet the above-mentioned requirements. Medical adhesive assemblies are "temperature-activated" (or "temperature-sensitive") in that the medical adhesive assemblies are either: (1) "pre-positionable" i.e., they present a surface which is substantially nontacky below skin temperature and permits accurate placement on the skin before absorbing enough heat from the skin to become aggressively tacky. Thereafter, they adhere to the skin in the manner of a normal PSA; (2) removable by chilling, i.e., at skin temperatures, they exhibit string adhesion to the skin but lose adhesion upon cooling; or (3) a combination of embodiments (1) and (2). All of these embodiments involve an adhesive composition which displays a rapid transition between a tacky state and a substantially nontacky state. For example, if the adhesive assembly is heated up above the normal skin transition temperature, the adhesive component will become aggressively tacky and stick to almost anything with which it comes in contact, i.e., it will form a stronger bond with a release liner if one is present. However, when the assembly is cooled to several degrees below that skin transition temperature, the adhesive will lose adhesivity, permitting its removal from the liner and rapidly revert to its nontacky state.

First turning to the adhesive assemblies useful in medical applications, those assemblies comprise body members having a surface which is coated with a temperature-activated adhesive composition. The body member may be, for example, an EKG electrode, or other type of electrode, a flexible backing in the case of adhesive tape, a surgical dressing, bandaid, medicated bandaid, a transdermal drug delivery patch, or the like, or it may be a cast, splint, or similar immobilization device. Other skin contact applications are intended to be encompassed by the present invention as well, as the focal point of the invention is not on particular uses of the adhesive assemblies described and claimed herein but on the incorporation of a temperature-activated adhesive composition into different types of adhesive assemblies.

Preferred assemblies are in the form of tapes and bandages which keep water and bacteria out while allowing the exchange of water vapor. This can be accomplished in a number of ways but is generally obtained by starting with a backing layer having a moisture vapor transmission rate (MVTR) of above 500 g/m$^2$/day at 37° C. and relative humidity difference of 100% to 10%. The MVTR can be reduced by the adhesive. However, the backing substrate and adhesive can be chosen so that the MVTR of the final assembly is more than 100 g/m$^2$/day preferably more than 500 g/m$^2$/day. If the bandage is, for example, in a large rectangular shape, the adhesive can be applied along the edge in a strip-like fashion so that the adhesive will not affect the MVTR of the majority of the bandage where no adhesive is present.

Useful backing materials may be woven cloth treated to resist moisture; Gortex TM -type materials or polyether polyester thermoplastic copolymers having characteristic as described above. An example of a useful backing is known commercially as Hytrel TM which is manufactured by Dupont. Also useful are polyether polyamides such as Pebax TM manufactured by ATO Chemical Co., microporous polymeric materials such as Cellgard TM manufactured by Hoechst Cellanese and polyether polyurethanes such as Estane TM manufactured by Goodrich Chemicals Inc. The particular form of the backing used can be chosen by checking manufacturer specifications regarding MVTR and/or by testing the material using known testing methods such as the Payne Cup Method described herein. The thickness of the backing layer can, of course, have a substantial effect on the MVTR of the layer. A sheet of Estane TM having a thickness of about 25 $\mu$a will have a MVTR of about 1800 g/m$^2$/day and can be used as s backing layer in connection with the present invention. Other useful backing materials included 1,2-polybutadiene films sold by Japan Synthetic Rubber Company as RB810, RB820, and RB830 having a thickness of about 150 $\mu$m.

The above-described backing layer materials with skin-compatible MVTR can be used in connection with any of the three types of three medical adhesive assembly devices described below: (I) A prepositionable adhesive assembly which is initially substantially nontacky, i.e., at or below room temperature, but which becomes tacky relatively quickly upon application to skin; (II) an adhesive assembly which may or may not be tacky to start with, but which strongly bonds to skin and is capable of losing adhesion upon cooling; and (III) an adhesive assembly in which the characteristics of Embodiments (I) and (II) are combined, i.e., a temperature-reversible system which is initially substantially nontacky, strongly bonds to skin, and loses adhesivity upon cooling.

In Embodiment (I), the adhesive composition comprises a polymer which has a first-order transition temperature or melting point above room temperature (i.e., approximately 25° C. in most cases) but at or below skin temperature. By the terms "melting point" or "first order transition" as used herein is meant the temperature at which an equilibrium process causes certain portions of the polymer, initially aligned in an ordered array, to become disordered. By the term "freezing point" is meant the temperature at which an equilibrium process causes those certain portions of the polymer, initially disordered, to become aligned in an ordered array. Preferably, the first-order transition temperature or melting point will be in the range of about 20° C. to 37+ C., more preferably in the range of about 25° C. to 32° C. It is preferred that melting occur rapidly, i.e., over a relatively narrow temperature range, less than about 10 centigrade degrees, preferably less than about 5 centigrade degrees. In Embodiment (I), the adhesive assembly is substantially nontacky up until the moment of application, and becomes tacky upon contact with skin; no additional external activation of any sort is required. (Melting of most polymers can be monitored with the aid of a differential scanning calorimeter, or "DSC". Malting generally takes place over a 10 centigrade degree range, and onset of tack occurs at the onset of melting; the melting "point" of the polymers as described herein is actually the temperature at which melting begins. The strongest bonding occurs when the temperature is high enough to effect complete melting.)

In this embodiment, the adhesive is typically completely nontacky at room temperature, so that a bandage, wound dressing, or the like formulated with the adhesive composition can be applied, positioned and maneuvered about, if necessary, within a short period of time and without unwanted adhesion. In some cases, however, it will be preferred that the adhesive be slightly tacky at room temperature, so that a release liner may adhere to and protect the adhesive coating prior to use. Slight tack at room temperature may be achieved by combining the adhesive composition with standard pressure-sensitive adhesives or incorporation of tackifiers into the selected polymer.

In Embodiment (II), the adhesive composition comprises a polymer which provides for loss of adhesion upon simple chilling, e.g., by application of ice, a cold pack, or the like. In this embodiment, the polymer should have a freezing (or "crystallization") point lower than skin temperature, preferably in the range of about 10° C. to 28° C., more preferably in the range of about 15° C. to 25° C. It is also preferable that the polymer crystallize rapidly. To this end, seeding agents, or crystallization catalysts can be incorporated into the polymer which provide for rapid crystallization kinetics. In this embodiment, removal of the adhesive assembly from the skin is greatly facilitated; after use, adhesive tapes, bodies and the like may be readily removed by simple chilling, only slightly below their use temperature, without imparting undue trauma to the skin.

In Embodiment (III), the characteristics of the adhesive assemblies of Embodiments (I) and (II) are combined. That is to say, adhesive assemblies in this class display temperature-reversible adhesion; they are substantially nontacky initially, prior to use (at room temperature), they become tacky upon application to skin, and they rapidly lose tack and may thus be removed from skin by cooling. In this embodiment, it is preferred that the polymer of the adhesive assembly have a melting 10 point or first-order transition temperature within the range set forth for Embodiment (I), and a freezing or crystallization temperature within the range set forth for Embodiment (II).

Now turning to those embodiments which may have nonmedical, as well as medical applications, the present invention also encompasses the use of a "warm-activated" adhesive assembly (for purposes of convenience, designated "Embodiment (IV)" herein). As explained above, such an assembly is formulated with an adhesive composition that is normally nontacky but which may be rendered tacky when warmed just slightly above room temperature, preferably less than about 20 centigrade degrees above room temperature, more preferably less than about 15 centigrade degrees above room temperature, most preferably less than about 10 centigrade degrees above room temperature. Such an assembly is suitable for application to the skin, and is, in addition, useful in a number of other contexts.

In this case, again, it is desirable that the transition from nontacky to tacky occur over a relatively small temperature range, i.e., over a range of less than about 15 centigrade degrees, and not require activation above about 45° C. Temperatures of up to 37° C. may be obtained simply by contact with human skin while temperature of up to 45° C. are readily attained (by using, for example, a hair dryer). Activation temperatures greater than about 45° C. are not desirable for medical applications used on skin because skin will not tolerate a temperature much above that temperature.

The warm-activated adhesive assembly is particularly useful for sticking permanently to porous substrates after activation, even when the assembly is exposed to low temperatures for long periods of time. By "porous" substrates is meant, e.g., paper, cloth, wood, and the like, i.e., substrates that have a structure which allow for at least partial penetration of the activated adhesive composition.

In Embodiment (V), temperature-activated adhesive compositions are used to formulate "chill-off" labels or tape, i.e., labels or tape which stick aggressively to a substrate during a designated period of use but which may be readily removed upon chilling. This type of adhesive assembly addresses several needs in the art. First, it is clearly desirable to have a normally tacky pressure-sensitive adhesive which bonds well to a variety of substrates yet can be easily removed at a later time. This will be readily appreciated by most if not all consumers who find virtually all labels impossible to remove completely without considerable time, scraping, and/or use of solvents or other chemicals. In addition, in the painting of substrates it is common to use tape to mask-off area that is not to be painted, and to later remove the tape. If the tape sticks poorly, paint may bleed into the masked area; if the tape sticks too strongly it may remove a portion of the substrate—also, clearly, an undesirable result. In still another example, it is desirable to affix labels or price tags to articles of commerce such that they cannot be readily removed. This is currently done by using adhesives and labels selected such that removal of the label results in cohesive failure of the label material. While this serves a "tamper-resistant" function, this type of label will be difficult to remove even when removal is proper, i.e., after purchase.

The "chill off" adhesive assembly of the invention, which can be rendered significantly less strongly bonded by simple chilling, thus addresses each of the aforementioned needs. An adhesive is used which is a normally tacky pressure-sensitive adhesive, but which loses a significant portion of its adhesion or bond strength to the substrate when cooled to a low temperature, thus allowing the adhesive assembly—i.e., the label, tape, or the like—to be readily removed from the substrate without leaving any residue and without need for scraping, solvents, or other chemicals. Such an adhesive composition can be used on many types of substrates, e.g., metal, glass, plastic, and the like.

The term "tack" as used hereinabove is intended to designate the tacky or sticky nature of the adhesive compositions. Tack can generally be determined by what is referred to as the thumb test in which the thumb makes rapid and reversible contact with the surface being considered to determine the tacky or sticky nature of the surface. A substantially more accurate and reproducible test for tack is designated D2979 by the American Society for Testing and Materials. In this test which employs a Polyken TM instrument, values are given in grams of force required to remove the end of a stainless steel rod, 5.0 mm in diameter, from the surface of an adhesive coated assembly. Prior to the removal, the rod approaches the surface at a speed of 10 mm per second and makes contact with the adhesive for a prescribed period of time. The actual time of contact is variable and discretionary. (In obtaining the values reported herein, a half-second dwell time was used.) The units of measure are given in grams.cm/sec and are the ones to which a plurality of the tack values used in the present specification refer. The Tack Rolling Ball Test (TRBT) designated as D3121 by the above Society and PSTC-6 (revision 8/85) by the Pressure Sensitive Tape Council is also ideally suited for accurately and reproducibly measuring tack over wide temperature ranges. This test is described in the Experimental section of this application, below.

The terms "tack" and "tacky" are qualitative. The tack of an adhesive film coating is affected by its thickness, especially when the coating is less than about 0.005 in thickness. Generally, tack increases linearly with thickness. In order to make a more quantitative evaluation between different samples made with different coating thicknesses, tack values can be (and have been in this application) normalized to values which would be expected had that sample been cast or otherwise applied at a thickness of 0.001 inch.

The terms relating to the normalized value properties of an adhesive coating obtained by either the PKI or TRBT tack determination method can be verbally described as "substantially nontacky" "slightly tacky" and "tacky". These terms are intended to relate to approximate values, respectively: (1) a tack value which is the minimum limit of the instrument or less than about 25 g.cm/sec of force; (2) a tack value between that described in (1) to about 100 g.cm/sec of force; and (3) a tack of at least about 100 g.cm/sec of force.

The term "bond strength" between an adhesive coated article and the substrate to which it is joined is defined as the force required to separate those components.

The term "peel" as used hereinabove is intended to define the bond strength between an adhesive coated article and the substrate to which it's joined when those components are separated at a rate of 12 inches/min and where the angle between separated components approximates 180°. The peel strength of an adhesive film coating is also affected by its thickness, especially when the coating is less than 0.005 inches thick. Generally, peel strength of any particular adhesive increases linearly with the square root of thickness. In order to make a more quantitative evaluation between different samples made with different coating thicknesses, peel strength values can be (and have been in this application) normalized to values which would be expected had that; sample been cast or otherwise applied at a thickness of 0.001 inch.

The polymer in each of Embodiments (I), (II) and (III), (IV) and (V) is preferably a crystallizable polymer or a functional equivalent of a crystallizable polymer having a weight average molecular weight in the range of about 20,000 to 2,300,000 Daltons, typically 100,000 to 1,300,000 Daltons, most typically 250,000 to 1,000,000 Daltons. By polymers which are "functionally equivalent" to crystallizable polymers for purposes of the present invention, applicant intends to include polymers which exhibit the temperature-dependent adhesion properties described above. Crystallizable polymers which may be used in the adhesive composition include both side-chain crystallizable and main-chain crystallizable polymers, the difference being that the former class of compounds contain crystallizable side-chain moieties, and the latter class are rendered crystallizable by their backbone structure. Depending on the embodiment, the polymer selected for incorporation into the adhesive assembly will comprise different monomers which provide the composition with the desired phase transition temperature, bond strength, and tack. The adhesive composition may also be formulated so as to contains blends of two or more different polymers as described herein. An assembly of the invention such as a medical tape may have different adhesives coated thereon in two or more layers over each other and may be coated continuously or sporadically in regular or irregular patterns.

Side-chain crystallizable polymers, sometimes called "comb-like" polymers, are well-known and available commercially. These polymers are reviewed in *J. Polyreox Sci.: Macromol. Rev.* 8:117–253 (1974), the disclosure of which is hereby incorporated by reference. In general, these polymers contain monomer units X of the formula:

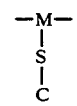

wherein M is a backbone atom, S is a spacer unit and C is a crystallizable group. These polymers generally have a heat of fusion (WH$_f$) of at least about 20 Joules/g, preferably at least about 40 Joules/g. The polymers will contain 50 to 100 wt. % monomer units represented by "X". If the polymer contains less than 100% X, it will in addition contain monomer units which may be represented by "Y" or "Z" or both wherein Y is any polar or nonpolar monomer or mixture of polar or nonpolar monomers capable of polymerizing with X and/or Z, and wherein Z is a polar monomer or mixture of polar monomers. These polar monomers—e.g., polyoxyalkylenes, acrylates including hydroxyethylacrylate, acrylamides and methacrylamides—will typically increase adhesion to most substrates. If the polar species "Z" is acrylic acid, it is preferred that it comprise about 1–10 wt. % of the polymer.

The backbone of the polymer (defined by "M") may be any organic structure (aliphatic or aromatic hydrocarbon, ester, ether, amide, etc.) or an inorganic structure (sulfide, phosphazine, silicone, etc.), and may include spacer linkages which can be any suitable organic or inorganic unit, for example ester, amide, hydrocarbon, phenyl, ether, or ionic salt (e.g., a carboxyl-alkyl ammonium or sulphonium or phosphonium ion pair or other known ionic salt pair).

The side-chain (defined by "S" and "C") may be aliphatic or aromatic or a combination of aliphatic and aromatic, but must be capable of entering into a crystalline state. Common examples are: linear aliphatic side-chains of at least 10 carbon atoms, e.g., $C_{14}$-$C_{22}$ acrylates or methacrylates, acrylamides or methacrylamides, vinyl ethers or esters, siloxanes or alpha olefins; fluorinated aliphatic side chains of at least 6 carbons; and p-alkyl styrene side chains wherein the alkyl is of 8 to 24 carbon atoms.

The length of the side-chain moiety is usually greater than 5 times the distance between side-chains in the case of acrylates, methacrylates, vinyl esters, acrylamides, methacrylamides, vinyl ethers and alpha olefins. In the extreme case of a fluoroacrylate alternate copolymer with butadiene, the side-chain can be as little as two times the length as the distance between the branches. In any case, the side-chain units should make up greater than 50% of the volume of the polymer, preferably greater than 65% of the volume.

Specific examples of side-chain crystallizable monomers are the acrylate, fluoroacrylate, methacrylate and vinyl ester polymers described in *J. Poly. Sci.* 10.3347 (1972); *J. Poly. Sci.* 10:1657 (1972); *J. Poly. Sci.* 9:3367 (1971); *J. Poly. Sci.* 9:3349 (1971); *J. Poly. Sci.* 9:1835 (1971); *J.A.C.S.* 76:6280 (1954); *J. Poly. Sci.* 7:3053 (1969); *Polymer J.* 17:991 (1985), corresponding acrylamides, substituted acrylamide and maleimide polymers (*J. Poly. Sci.: Poly. Physics Ed.* 11:2197 (1980); polyalphaolefin polymers such as those described in *J. Poly. Sci.: Macromol. Rev.* 8:117-253 (1974) and *Macromolecules* 13:12 (1980), polyalkyl vinylethers, polyalkylethylene oxides such as those described in Macromolecules 13:15 (1980), alkylphos phazene polymers, polyamino acids such as those described in *Poly. Sci. USSR* 21:241, *Macromolecules* 18:2141, polyisocyanates such as those described in *Macromolecules* 12:94 (1979), polyurethanes made by reacting amine- or alcohol-containing monomers with long-chain alkyl isocyanates, polyesters and polyethers, polysiloxanes and polysilanes such as those described in *Macromolecules* 19:611 (1986), and p-alkylstyrene polymers such as those described in *J.A.C.S.* 75:3326 (1953) and *J. Poly. Sci.* 60:19 (1962).

Of specific utility are polymers which are both relatively polar and capable of crystallization, but wherein the crystallizing portion is not affected by moisture. For example, incorporation of polyoxyethylene, polyoxypropylene, polyoxybutylene or copolyoxyalkylene units in the polymer will make the polymer more polar, improving adhesion to moist skin.

Hydrophilic monomers are beneficially added to the polymer if it is desired to increase the MVTR properties of the adhesive. Commonly used hydrophilic comonomers include acrylic acid, acrylamide, hydroxy alkyl (meth)acrylates such as hydroxy ethyl acrylate, hydroxy ethyl methacylate and hydroxy butyl acrylate, alkoxy (meth)acrylates such as ethoxy ethyl acrylate, ethoxy ethoxy ethylacrylate, ethyltriglycol methacrylate, 3-methoxy butylacrylate and the like. A preferred class of high MVTR inducing monomers are derivatives of polyethylene glycol of with molecular weights ranging from 50 to 5,000. Commonly these units may be incorporated either into the backbone or as pendant groups.

Moisture vapor transmission rates and/or absorptive properties of the adhesive may be modified by the incorporation of soluble or insoluble hydrophilic materials, for example by addition of carboxymethyl cellulose, guar gum, carragean, cellulose based or synthetic fibers and the like.

In a particularly preferred embodiment herein, in the above structure, —C is selected from the group consisting of —$(CH_2)_n$—$CH_3$ and —$(CF_2)_n$—$CF_2H$, where n is an integer in the range of 8 to 20 inclusive, —S— is selected from the group consisting of —O—, —$CH_2$—, —(CO)—, —O(CO)— and —NR— where R is hydrogen or lower alkyl (1-6C) , and —M— is —[($CH_2$)$_m$—CH]— where m is 0 to 2.

Typical "Y" units include linear or branched alkyl or aryl acrylates or methacrylates, alpha olefins, linear or branched alkyl vinyl ether or vinyl esters, maleic esters or itaconic acid esters, acrylamides, styrenes or substituted styrenes, acrylic acid, methacrylic acid and hydrophilic monomers as detailed in W084/0397, cited supra.

In addition to the above-described monomer units "M-S-C" monomer structures given by

may in addition, or in the alternative, be present in the polymer. "D" is a hydrophilic polyether chain such as a polyoxyalkylene chain (e.g., polyoxyethylene) which, in contrast to "C" may or may not be crystallizable "D" preferably has a molecular weight higher than about 100 Daltons.

It is important in the case of polyolefins, which can exist in a plurality of tactic forms, that in order to effect the sharpness of transition between tacky and nontacky states the tacticity of the polymer must be carefully selected. The polymer can be present in a singular configuration, i.e., either atactic, syndiotactic or isotactic, but not in a mixture of tacticities unless their melting points opportunistically coincide. Having a mixture of various tacticpolymers with different melting points will broaden the transition and cause the resultant polymer to exhibit sluggish adhesive property changes over a narrow temperature range.

Preferred main-chain crystallizable polymers include water-insoluble polyalkylene oxides, lower alkyl polyesters and polytetrahydrofuran.

The crystallizable polymer, whether side-chain or main-chain crystallizable, may or may not be cross-linked. Cross-linking the adhesive composition as well as employing high molecular weight polymers will, in general, result in a material that exhibits decreased melt flow and greater cohesive strength than non-cross-linked and low molecular weight materials. Because the adhesive composition may be used at temperatures above the melting point of the polymer, low melt flow is desirable so that the adhesive will not migrate, flow or transfer to the substrate surface (i.e., in contrast to conventional "hot-melt" adhesives). Adhesive compositions with sufficient cohesive strength to prevent cohesive failure is thus desirable. Low melt flow and suitable cohesive strength may be achieved by other means such as the addition of suitable comonomers (e.g., high Tg monomers), by the use of block copolymerization or other art-known methods, or the inducement of crosslinking before, during or after preparation of the adhesive assembly.

A variety of methods are available to produce cross-linked crystallizable materials. A network copolymer can be prepared by polymerizing a crystallizable monomer and a multifunctional monomer either in one or two steps. A one-step process may be used to form an adhesive in place, while a two-step process is useful where an intermediate processing step is necessary. A variety of multifunctional monomers (di-, tri- or multifunctional acrylic or methacrylic esters, vinyl ethers, esters or amides, isocyanates, aldehydes, epoxies and the like) are known in the art. These multifunctional monomers can be used in a one- or two-step process depending on the desired result. Ionizing radiation, for example beta or gamma radiation, peroxides, silanes, or similar cure agents, can be used to cross-link a preformed crystallizable polymer with or without added comonomers. Ionic cross-links can be formed by, for example, reacting an acidic polymer site with a di- or trivalent metal salt or oxide to produce a complex which serves as a cross-link site. Likewise, organic salts or complexes can be prepared by methods known in the art.

If the material is cross-linked to too great an extent, crystallinity and/or tack may be decreased to the point that the desirable temperature activated properties are lost. To optimize the aforementioned factors, cross-linking should be in the range of about 0.01 percent to 5 mole percent and preferably 0.05 to 1 mole percent. The cross-linked polymers will normally have a heat of fusion of at least about 20 Joules/g, and preferably at least 30 Joules/g.

Effective cross-linking may also be obtained by physical methods. For example, a block copolymer containing a crystallizable portion and a second portion which exhibits a glass transition or melting point higher than the crystallizable polymer may be prepared wherein the entire mass exhibits mechanical stability above the melting point of the crystallizable polymer but below the transition of the second polymer.

As noted earlier, it is also desirable that the adhesive composition be formulated with a polymer or mixture of polymers selected such that the first-order melting transition of the composition occurs over a range narrower than about 15° C., preferably narrower than about 10° C. It is also preferred that the melting transition occur between about 5° C. and about 50° C. In addition, the tack of the composition must develop within less than a minute when it is raised above the melting range and then, without contacting any substrate, revert to the nontacky state when the temperature is lowered a few degrees below the melting range. This reversal should take less than about 5 minutes. The latter tack value (PKI) is preferably less than about 25 g.cm/sec or the minimum limit of the tack measuring instrument.

The adhesive compositions useful herein may include, in addition to one or more polymers as described above, conventional additives such as tackifiers (wood rosin, polyesters, etc.), antioxidants, fibrous or nonfibrous fillers, colorants, and the like. It is also possible to include additional adhesives, providing that the overall temperature sensitivity profile is not significantly affected. It is preferred that the amount of crystallizable polymer in the adhesive composition be in the range of about 40 wt. % to about 100 wt. %.

coating of the body members, or substrates, with the temperature-activated adhesive composition (i.e., to provide tapes, labels, or the like) may be done in any number of ways, e.g., by spray deposition, painting, dipping, gravure printing, rolling, or the like. The adhesive composition may also be applied by transfer from a release sheet, i.e., in a manner similar to that involved in transfer printing. The composition may be applied neat, or in a suitable solvent or as an emulsion or latex. Alternatively, a mixture of the appropriate monomers and additives may be applied directly to a substrate and cured in place by heat, irradiation, or other suitable art-known processes.

In adhesive tapes and sheets, specifically, the backing onto which the temperature-activated adhesive composition is coated may comprise any number of backings which are well-known in the medical or surgical fields. Thus, the backing may be a woven or nonwoven fabric, paper, or a synthetic film. Depending on the specific medical application, the backing may or may not be occlusive.

It will be appreciated by those skilled in the art that the temperature-activated adhesive compositions and adhesive assemblies described herein are useful in a variety of medical applications, i.e., in binding adhesive tape, bandaids, immobilization devices, transdermal drug delivery devices, surgical dressings, EKG electrodes, etc., to skin.

The foregoing description as well as the examples which follow are intended to illustrate and not limit the scope of the invention.

EXAMPLES

Experimental:

Melting temperatures and heats of fusion were determined using Differential Scanning calorimetry (DSC) at a heating rate of 10° C./min. Heats of fusion ($WH_f$) are expressed in J/g.

Crystallization temperatures were also determined by DSC, at a cooling rate of 10° C/min.

Peel strength was measured by two different methods, one employed an Instron Materials Testing Instrument (IMTI), the other, an Instrumentors Slip/Peel Tester (ISPI).

IMTI Peel strength:

Peel strength was measured as follows. A solution (50% solids) of adhesive formulation was prepared in tetrahydrofuran, cast onto a flexible PVC film, and air-dried at 70° C. for 30 minutes. A 1" wide strip was covered with a 1" uncoated strip of the PVC film. The assembly was lightly pressed together at a temperature of 37° C. Average peel strength was measured at 10"/min using an Instron materials testing instrument equipped with a variable temperature chamber.

ISPI Peel Strength:

Peel strength was measured as follows. An Instrumentors, Inc. SP-102B Slip/Peel Tester was used according to the test procedure designated as PCTC-1 (revision 8/85) by the Pressure Sensitive Tape Council and was calibrated and operated according to the instruction manual accompanying the instrument. In addition, sample preparation included: coating, generally, was cast from a heptane/methyl ethyl ketone solution (90:10) containing between 15% and 45% solute (adhesive). All coatings were dried, in an oven for 18 to 24 hours @ 50° C. Dried coatings were cooled for 0.50 to 0.75 hours at room temperature. Individual specimens were cut lengthwise (generally 0.5 in. × 5.0 in. strips) in the direction of extrusion (of the backing substrate). Each specimen was gauged for coating thickness to the nearest 0.1 mil. At least three (3) points on each specimen were measured and the average of these points were considered the thickness value. Each testing specimen did not have greater than 0.25 mil variation from the thinnest point to the thickest point and the variation between thickness values of all the testing specimens did not exceed 0.25 mils. The average of the specimen thickness values (to the nearest 0.001 inch) was the reported coating thickness. The peel test was conducted as soon as possible after measuring coating thicknesses; The testing substrate surface was a 0.012 inch thick polyurethane film of Tuftane 410 (Lord Corporation, Erie, Pa.) which was secured to the temperature controlled platen by means of double sided carpet tape. Each specimen remained on the testing surface for 5 minutes before testing at the prescribed temperature of testing. Ten specimens were tested at each specific temperature. Each specimen was rolled with a 4.5 pound rubber roller immediately after contact with testing surface. The roller traveled over the surface of the specimen at a rate of 12 inches/min in both directions. The average peel force & terminal surface temperature was recorded.

Tack values were measured by three different methods. One employs a Surface Texture Analyzer (STA); another, a Polyken TM Instrument (PKI) and the third, a Tack Rolling Ball Test (TRBT).

STA Tack measurement:

Tack was measured using a Surface Texture Analyzer (a Voland-Stevens LFRA Texture Analyzer). The probe was allowed to contact the adhesive for 10 seconds and was then withdrawn at 0.2 mm/sec. Tack values reported herein are the average maximum reading.

PKI Tack Measurement:

Tack was measured by the procedure designated D2979 by the American Society for Testing and Materials. In this test, which employs a Polyken TM instrument, values are given in grams of force required to remove the end of a stainless steel rod, 5.0 mm in diameter, from the surface of an adhesive coated assembly. Prior to the removal, the rod approaches the surface at a speed of 10 mm per second and makes contact with the adhesive for a prescribed period of time. The actual time of contact is variable and discretionary. We chose to use a half second dwell time. Testing was performed generally at room temperature. The units of measure are in grams.cm/sec.

TRBT Tack Measurement:

Tack was measured by the Rolling Ball Test designated as D3121 by the American Society for Testing and Materials and PTSC-6 (revision 8/85) by the Pressure Sensitive Tape Council. The technique was ideally suited for accurately and reproducibly measuring tack over wide temperature ranges. This test uses a designated 21 30' incline, a 7/16 diameter steel ball and a temperature controlled level, hard and smooth plate upon which a layer of Scotch TM 3M brand double sided carpet tape (23-8049) is mounted. The test strips are placed on top of the tape with the adhesive side up, covered with release liner and rolled with a standard 4.5 lb rubber wheel. After the test strip comes into temperature equilibrium with the plate, the release liner is removed and the ball is released from the top of the inclined plane. The ball rolls down the plane, gathers momentum and encounters the horizontal test strip. At which point, the rolling ball decelerates (according to the degree of tack) travels a specific distance and stops. The average of stopping distance measurements (between the end of the inclined plane and the center of the ball) are recorded. Five tests determine the average. In order to maintain a consistency of tack units, we have made the following empirical conversion from TRBT (cm of travel) to units of those produced by the Polyken TM test instrument.

$$Tack(g.cm/sec) = k/cm \text{ of travel} + 7.25 \text{ g.cm/sec}$$

where
$k = 735 g.cm2/sec$

Measurement of tack temperature: A 1"×1" test sample was bonded face up to a metal plate with double sided adhesive tape and the metal plate was placed in a temperature controlled oven and allowed to equilibrate at the selected temperature for 10 minutes. Tack was tested by lightly pressing a 1 cm diameter plastic rod onto the surface of the adhesive for 1 second and then removing. After testing at the lowest temperature, the oven temperature was increased by 2° C. and test repeated. The tack temperature is defined as the minimum temperature at which a noticeable tack was first observed.

MVTR Determination via the Payne Cup Method

Materials to be tested are cut into disc shapes and clamped over Payne Permeability Cups (flanged metal cups) using sealing rings and screw clamps. The flanges on the cups are coated with 30 g/m² of an acrylic adhesive. The samples have 10 cm² of exposed surface area. Each cup contains approximately 10 ml of distilled water.

The cups are weighted and placed in a fan assisted oven which is maintained at 37°±1° C. The relative humidity within the oven is maintained at approximately 10% by placing 1 kg of anhydrous 3–8 mesh calcium chloride on the floor of the oven.

The cups are removed after 24 hours, allowed to cool for 20 minutes and re-weighed. The MVP of the test material is calculated from the weight loss and expressed in units of grams of weight per square meter per day, i.e. 24 hours.

EXAMPLE 1

A polymer was prepared by combining 10 g of hexadecyl acrylate, 2 g of ethyl acrylate, 15 ml of deoxygenated toluene, and 0.06 g of AIBN, and heating at 60° C. under a nitrogen atmosphere for 12 hours. The resulting mass was extracted with ethanol and dried in vacuo to yield a rubbery mass. Thermal analysis showed that this material had a melting point of 34° C. a freezing point of 26° C., and a heat of fusion of 64 J/g. A sample of this material was heated to 70° C. and pressed into a 0.001"-thick film. A sample of the film was placed onto the adhesive side of a commercial plastic-backed PSA tape and stored at 25° C. The resulting taps was nontacky to the touch and exhibited no tack or adhesion to paper at room temperature. When the tape was placed on the wrist of a human subject, however, it became tacky almost instantly and exhibited good adhesion. When removed from the skin and kept at room temperature, the tape quickly lost its tack and adhesive properties.

EXAMPLE 2

Five percent acrylic acid, 5% ethylacrylatehexadecylacrylate copolymer (1 g) was mixed with 1 ml of toluene and 0.004 g XAMA 2 (Virginia Chemicals, Portsmouth, Va.) as cross-linking agent. The material was allowed to stand two days at 80° C. at which point it was more viscous. More toluene was added to make the solution spreadable. The mixture was then spread onto clear PVC film, dried at 80° C. for 1 hour, and allowed to cool. The composition displayed excellent adhesion to skin at body temperature and was easily removed with a cool, damp paper towel. This adhesive exhibited no tack at room temperature.

EXAMPLE 3

Sixteen grams of hexadecylacrylate, 3 grams of isodecylacrylate (Sartomer), 1 gram of acrylic acid, 0.100 gram of AIBN was combined with 30 ml of toluene, purged with nitrogen and reacted for 11 hours at 70° C. The resulting solution was precipitated into methanol and dried. Test samples were prepared by solution coating a 50% solids solution of the polymer in tetrahydrofuran onto a PVC backing and drying at 50° C. The dry thickness of the resulting adhesive was approximately 0.0025 cm. Crosslinked samples were prepared by addition of XAMA 2 to adhesive solution prior to coating and drying.

STA tack and IMTI adhesive strength were measured at 20° C. and 39° C. as shown in Table I.

TABLE I

| Cure (% w/w) | TACK(g/cm$^2$) (20° C.) | TACK(g/cm$^2$) (39° C.) | PEEL STRENGTH (g/cm) (20° C.) | PEEL STRENGTH (g/cm) (39° C.) |
|---|---|---|---|---|
| 0 | 0 | >100 | >4.5 | 7 |
| 0.75 | 0 | 12 | >4.5 | — |
| 0.35 | 0 | 15 | >4.5 | 21 |

EXAMPLE 3a

The following polymers were prepared using heptane as the solvent, a reduced amount of catalyst (AIBN) and longer reaction times. The symbols C16, C6 and AA, used in Table II below, refer to the monomers hexadecylacrylate, hexylacrylate and acrylic acid respectively.

TABLE II

| Sample | Monomer Content (%) C16 | C6 | AA | Mol. Weight Mw (K = 1000) |
|---|---|---|---|---|
| 555 | 83.5 | 12.5 | 4 | 914K |
| 557 | 83.5 | 12.5 | 4 | 862K |
| 558 | 83.5 | 12.5 | 4 | 739K |
| 563 | 83.5 | 12.5 | 4 | |
| 639 | 84 | 13 | 3 | 401K |
| 999 | 25 | 72 | 3 | 999K |

A DSC analysis of the first 5 samples revealed peak melting temperatures between about 29° C. to 31.4° C. Of those samples, no sample began melting before about 27.5° C. and all samples were totally disordered when the temperature reached 35° C. Enthalpy values (heats of fusion) ranged between 44 and 52 J/g. Sample 999 had no detectable first order transition above 5° C.

EXAMPLE 3b

A blend of polymers was used to make an adhesive composition, as follows:

TABLE III

| Ingredient or Sample Number | Parts by Weight (grams) |
|---|---|
| 555 | 12.73 |
| 557 | 13.26 |
| 558 | 21.93 |
| 563 | 9.02 |
| 639 | 39.62 |
| Lauric Acid | 3.39 |

The adhesive properties of this blend are described in Example 3d.

EXAMPLE 3c

A dodecene polyolefin was prepared as follows: Into a dried, 2 liter reaction flask was added 100 ml of dry heptane under a blanket of dry nitrogen. Catalyst was prepared by adding 0.7 ml of TiCl4 and 3 ml of Al(C$_2$H$_5$)$_3$, to the solvent. The system was stirred for one hour at room temperature (a bath was used to afford a constant temperature) and purged with dry nitrogen to remove all traces of Oxygen. Next, 240 ml (180 g) of dodecene was added to the flask in an anhydrous manner as practical. The polymerization reaction was run for 5 hours. At the end of this time, the reaction was quenched with ethanol. The polymer precipitated and the solution was decanted. The precipitate was washed with fresh alcohol and then dissolved in toluene at temperatures not exceeding 90° C. That solution was again precipitated by adding an excess of ethanol. That material was filtered and dried in a vacuum oven at room temperature. The final dried product weighed 89 grams. The viscosity of the polymer was measured in cyclohexane. The values of the inherent and reduced specific viscosities were extrapolated to zero concentration and found to be 4.22 and 3.79 respectively. The intrinsic viscosity was taken as the average of these values. Therefore, $\eta = 4.01$ deciliters/g. The DSC analysis revealed that the polymer sample exhibited a broad melting peak beginning at about 31° C. and extending to about 52° C. Enthalpy (heat of fusion) value was 28 J/g.

EXAMPLE 3d

The following experiment was run to demonstrate how the temperature of the adhesive coated article would affect the tack of various adhesives. A commercial 3M ™ Steri Drape 1040 surgical incise drape was used as a control. The adhesive coating was measured to be 0.001 inch thick. The product of Example 3b was cast on a dupont Hytrel ™ backing using a 90:10 mixture of heptane:methylethyl ketone as a solvent. The thickness of the dried adhesive coating was 0.00175 inch thick. In order to normalize and compare the tack values to the standard 3M control, the values of tack were reduced by a value of 1/1.75. The product of Example 3c was cast on Mylar polyester film from a solution of heptane. The thickness of the dried adhesive coating was 0.00250 inch thick. In order to normalize and compare the tack values with the standard 3M control, the values of tack were reduced by a factor of 1/2.5. Tack values were measured at various temperatures. The temperature of the samples were never brought above the temperature at which they were measured. Table IV below lists the tack values for the control and normalized tack values of the samples. (All values are reported in g.cm/sec units.)

TABLE IV

| Temperature (C) | 3M Control | Example 3b | Example 3c |
| --- | --- | --- | --- |
| 23 | | | 14.66 |
| 25 | 90.77 | | 14.66 |
| 26 | 123.92 | 21 | 14.66 |
| 27 | 72.29 | 21 | 14.66 |
| 28 | 52.62 | 26.62 | 15.25 |
| 29 | 71.16 | 211.26 | 29.07 |
| 30 | 97.99 | 273.43 | 38.77 |
| 31 | 75.31 | 297.71 | |
| 32 | 57.94 | | 59.05 |
| 35 | | 470.82 | 57 |
| 40 | | | 84.04 |
| 45 | | | 390.2 |

The data shows that the control is always tacky or slightly tacky at the temperature of the measurement and was not significantly affected by that temperature. The multitactic polyolefin of Example 3c was nontacky below 28° C., became slightly tacky when the temperature was raised above 28° C. and then became progressively more and more tacky as the temperature was raised to 45° C. In contrast, the blend in Example 3b was nontacky below 28° C. and then became tacky above 28° C.

Nine grams of the adhesive material produced in example 3b was admixed with 1 gram of polymer sample 999 listed in example 3a in a 90:10 mixture of heptane:methylethylketone solvent. The solution was cast onto backing as described in example 3d. The final dried thickness was 0.001 inch. When tested for tack, a value of 525 g.cm/sec was obtained.

EXAMPLE 3e

An experiment was run to demonstrate the time decay of tackiness after the samples were heated to 70° C. and then quenched to 23° C. Fresh samples, prepared and described in Examples 3b and 3c, were used for this study. Samples were conditioned at 70° C. for 2 hours after mounting. All the tack values were measured at 23° C. Table V below lists the normalized tack values and the logarithm of the normalized tack values of the samples.

TABLE V

| Time (hours) | Example 3b | Log Example 3b | Example 3c | Log Example 3c |
| --- | --- | --- | --- | --- |
| 0.03 | 28.14 | 1.45 | >400.00 | 2.60 |
| 0.08 | 20.94 | 1.32 | >400.00 | 2.60 |
| 0.17 | 20.94 | 1.32 | >400.00 | 2.60 |
| 0.50 | 20.94 | 1.32 | >400.00 | 2.60 |
| 1.00 | 20.94 | 1.32 | >400.00 | 2.60 |
| 2.00 | 20.94 | 1.32 | >400.00 | 2.60 |
| 5.00 | 20.94 | 1.32 | >400.00 | 2.60 |
| 8.00 | 20.94 | 1.32 | 172.84 | 2.24 |
| 24.00 | 20.94 | 1.32 | 94.78 | 1.98 |
| 48.00 | 20.94 | 1.32 | 90.40 | 1.96 |
| 72.00 | 20.94 | 1.32 | 75.85 | 1.88 |
| 120.00 | 20.94 | 1.32 | 55.78 | 1.75 |
| 126.00 | 20.94 | 1.32 | 53.07 | 1.72 |
| 127.00 | 20.94 | 1.32. | 36.58 | 1.56 |
| 144.00 | 20.94 | 1.32 | 32.30 | 1.51 |
| 152.00 | 20.94 | 1.32 | 39.65 | 1.60 |
| 169.00 | 20.94 | 1.32 | 33.98 | 1.53 |
| 177.00 | 20.94 | 1.32 | 30.48 | 1.48 |
| 192.00 | 20.94 | 1.32 | 40.12 | 1.60 |
| 199.00 | 20.94 | 1.32 | 22.55 | 1.35 |
| 200.00 | 20.94 | 1.32 | 27.60 | 1.44 |
| 216.00 | 20.94 | 1.32 | 22.90 | 1.36 |
| 240.00 | 20.94 | 1.32 | 21.16 | 1.33 |
| 247.00 | 20.94 | 1.32 | 15.60 | 1.19 |
| 248.00 | 20.94 | 1.32 | 14.66 | 1.17 |

The data show that a high degree of tack is retained by sample 3c for several days. After 10 days, the 3c samples regain their non-tacky state. In contrast, the 3b samples regain their non-tacky state within 0.08 hours or approximately, 5 minutes.

EXAMPLE 3f

An experiment was run to show that the adhesive compositions of the present invention will rapidly form good bonds to skin-like substrate (Tuftane 410), but only from a few degrees below skin temperature and above. In contrast, conventional PSA do not allow this temperature sensitive behavior. Peel strength measurements differentiate these behaviors. In the first set, the samples were never brought above the temperature at which they were affixed and measured. In a second set of experiments, a demonstration was achieved showing the reduction of bond strength after cooling the adhesive union (backing-adhesive-substrate) to a temperature several degrees below skin temperature (20° C.). The adhesives were actually affixed to the substrate in the range of temperatures used in the first set of experiments before the unions were cooled to 20° C. for 5 minutes. The peel strengths were then measured. Table VI lists the normalized peel strength values (grams/cm) for both sets of experiments including the commercial 3M TM Steri Drape 1040 surgical incise drape control. The terms "@ affix temp" and "@ 20° C." refer to the temperature of the union when the bond was made and the peel test was performed, respectively.

TABLE VI

| Affix Temperature (C) | Sample 3b @ Affix Temp | Sample 3b @ 20° C. | 3M Control @ affix Temp | 3M Control @ 20° C. |
| --- | --- | --- | --- | --- |
| 38.0 | | 30.00 | | 111.67 |
| 37.1 | 79.28 | | | |
| 37.0 | | | 87.36 | |
| 36.0 | | 28.73 | | 107.74 |
| 34.0 | 67.68 | | | |
| 33.8 | | | 89.55 | |
| 33.0 | | 11.34 | | 107.85 |
| 32.0 | 67.69 | | 90.69 | |
| 31.0 | | 12.85 | | 99.17 |
| 30.2 | | | 89.88 | |
| 30.1 | 52.95 | | | |
| 28.0 | 28.45 | | | |
| 27.9 | | | 100.16 | |
| 26.0 | 0.00 | | | |
| 25.7 | | | 101.81 | |
| 22.7 | 0.00 | | 110.98 | |

The results show that peel values for the 3M2 controls are relatively flat across the temperature range used for affixation and removal. No significant loss in peel strength occurs in those unions when they were cooled after affixation. In fact, the values appear to increase. On the contrary, the 3b samples demonstrate a substantial discontinuity in peel strength value above and below 28° C. transition point. In addition, the data reveal a significant reduction of peel strength when the unions are cooled to 20° C. after being affixed at any temperature above the 29° C. transition point.

EXAMPLE 4

Nineteen grams of pentadecylacrylate and 1 gram of acrylic acid were combined with 20 ml of heptane, 10 ml of ethylacetate and 0.070 grams of AIBN. Resulting solution was degassed and mixed at 70° C. for 17 hours. Polymer was isolated and dried in vacuo.

One gram of polymer and 0.003 grams Of XAMA 2 was dissolved into 2 ml of 1:1 heptane:ethylacetate and coated onto a 0.005 cm thick polyurethane backing (2103 AE, Dow Chemical, Midland Mich.) and dried at 80° C. for 15 minutes. The resulting tape was nontacky at room temperature but quickly adhered upon application to skin. During a 36 hour test on a human subject no disbondment of adhesive or film from skin was observed.

EXAMPLE 5

Two grams of a hexadecylacrylate, ethylacrylate, acrylic acid copolymer (76.5:20:2.5) was combined with 4 ml of 1:1 ethylacrylate:heptane solution and 0.0043 grams of XAMA 2. The resulting solution was coated onto urethane film and dried at 110° C. for 15 minutes. The obtained film was not tacky at 25° C. but bonded readily to a human subject. Samples showed no loss in adhesion when subjected to washing. During a 36 hour test no delamination of adhesive was observed.

EXAMPLE 6

The polymer of Example 3 alone and with 0.3% XAMA 2 was coated onto urethane backing and dried at 110° C. for 15 minutes. Both samples were nontacky at room temperature and quickly became tacky when contacted to human skin. Three 1"×1" test samples were applied to a test subject for seven hours. At that time it was observed that the non-crosslinked samples had lifted off from the skin around the edges and left a tacky residue on the skin when removed. The cross-linked sample in contrast stayed well bonded and left no tacky residue on the skin upon removal.

EXAMPLE 7

A copolymer of hexadecylacrylate, methylacrylate and acrylic acid (weight ratio 85:10:5) was prepared as in Example 3 above. A 1 gram sample was combined with 0.0024 grams of XAMA 2, 1 ml of heptane, 1 ml of ethyl acetate and coated onto a urethane backing and cured as in Example 6 above. Six 2.54 cm×2.54 cm test samples were applied to a human test subject for 26 hours. Three of the samples were removed at ambient temperature and three of the samples were chilled for 20 seconds with a cold Pepsi can prior to removal. All of the samples removed at ambient temperature resulted in visible amounts of skin being removed from the test subject. Two of the cooled samples showed no visible skin removal, while the third showed a very small amount of skin removal.

EXAMPLE 8

Forty-three grams of hexadecylacrylate, 6 grams of ethyl acrylate, 1 gram of acrylic acid and approximately 0.500 grams of AIBN were dissolved in 150 grams of ethyl acetate. The solution was purged with nitrogen and was heated at 45° C. for 24 hours and then at 60° C. for 2 hours. The viscous reaction product was precipitated into chilled ethanol as usual. After drying in a vacuum oven, the material was dissolved into heptane (30% solids). One weight percent of Zn stearate (based on polymer) was added to one half the solution.

The other half of the solution was used to cast film on a sheet of polyurethane (Tuftane). The resultant dried film was 0.00075 inches thick. Strips, 0.5×1.5 in$^2$ were cut from the sheet and mounted on the skin surface. They immediately were transformed from a non-tacky to an aggressively tacky strip. The strips were worn for 5 hours before they were removed at a rate of 1 cm/sec. A Chatillon DFG-2 Digital Gram Gauge was used to monitor the force needed for removal under normal conditions and after the sample was cooled with a cool damp cloth for several minutes. The uncooled removal required a peak force of about 0,273 Kg while the chilled removal required a peak force of about 0.132. The ratio of work needed for removal between the two methods of removal was calculated. That calculation showed that 2.25 more energy was required to remove the sample when it was at skin temperature than when it was chilled before removal.

The portion of the solution which contained the ionic cross-linking agent, Zn stearate, was cast on a similar backing as above. In this case, half of the samples were chilled with an ice cold can of soda. The average force required to remove the skin temperature sample was 0.156 Kg while the force to remove the chilled sample was only 0.036 Kg.

EXAMPLE 9

The cross-linked adhesive coated urethane of Example 5 above was applied to a sample of Tuftane 410 polymer film (Lord Corporation, Erie, Pa.) and warmed to 35° C. Material bonded well at this temperature but exhibited no adhesion when cooled to 20° C.

EXAMPLE 10

One gram of polyoctadecylmethacrylate acrylic acid copolymer (97.5:2.5) was combined with 1 ml of ethylacetate, and 0.0028 g of XAMA 2 and coated onto a urethane backing as in Example 6 above. Four 1"×1" samples were applied to a human test subject. After 24 hours two of the samples were removed at room temperature and two were first cooled with a cold Pepsi can and then removed. The two samples removed at ambient temperature showed visible skin removal while the samples which were first cooled showed no visible skin removal.

EXAMPLE 11

A polymer was prepared by polymerizing 4.25 g of hexadecyl acrylate, 4.24 g of tetradecyl acrylate 1.02 g of polyethyleneglycol monomethyl ether (DP=8) methacrylate and 0.50 g of acrylic acid in 20 ml of toluene containing 0.033 g of AIBN at 60° C. for 14 hours. A sample of the resultant polymer was combined with 0.25% XAMA 2 and coated onto a urethane backing as in Example 6 above.

The polymer made in accordance with the above-described procedure was coated on the urethane film disclosed in Example 6. The polymer coating was provided so as to provide a 1 mil thick film. The coated urethane film was then tested and found to have a MVTR of 450 g/m$^2$2/24 hours at 37° C. and a relative humidity difference of 100% to 10% when measured using the procedure of ASTM E 96–90. The polymer coated urethane film was non-tacky at room temperature and tacky at skin temperature.

EXAMPLE 12

Thirty-one grams of polytetrahydrofuran of M.W. 2900, (Scientific Polymer Products, Ontario, N.Y.) 1.85 grams of hexamethylene diisocyanate, 1 drop of dibutyltin dilaurate and 200 ml of dry toluene were combined and mixed for 24 hours and then 5 ml of ethanol was added with stirring. The resultant mixture was coated onto a glass slide, dried at 100° C. for 1 hour and then allowed to cool overnight. The resulting film was nontacky at 10° C. but tacky at skin temperature yet showed no tendency to flow.

After the polymer was produced in accordance with the above-described procedure the polymer was coated onto a flexible polymeric support backing sold under the trademark Hytrel 4056. The polymer was coated in an amount so as to provide a polymeric film having a thickness of 1 mil. The backing having the polymer coated thereon was tested and found to have a MVTR of 650 g/m²/24 hours at 37° C. and a relative humidity difference of 100% to 10%, when measured in accordance with the procedure of ASTM E 96-90.

EXAMPLE 13

One gram of polytetrahydrofuran (M.W. 2900) and 3.0 grams of the polymer solution of Example 12 were combined and coated onto a glass microscope slide, dried at 100° C. for 12 hours and allowed to cool.

EXAMPLE 14

To 20 ml of toluene were added 8.5 grams of hexadecylacrylate, 1.0 grams of polyethyleneglycol monomethyl ether (DP=S) methacrylate, 0.5 grams of acrylic acid and 0.0667 grams of AIBN. The solution was purged with nitrogen and heated at 60° C. for 14 hours. The product was precipitated into ethanol, filtered and dried under vacuum.

Test samples were prepared by solution casting. The solution contained 2 grams of the above polymer and enough ethyl acetate to bring the total weight up to 6 grams. To portions of this solution was added 0, 1, 2 and 3% of XAMA-2. Each solution was cast on polyvinyl chloride film using a 8.7 cm wide blade set at 3 mil. The films were air dried and then heated for 1 hour at 58° C. The width of the respective films were 8.1, 7.6, 7.3, 6.8 cm., indicating that crosslinking had occurred to various degrees.

Each of the samples became tacky above a temperature of 36° C. It was apparent that the order of tackiness decreased as the amount of XAMA-2 was increased.

EXAMPLE 15

A polymer solution was prepared as in Example 13 with hexadecyl acrylate, ethyl acrylate and acrylic acid in an 80:15:5 ratio. Testing was carried out as described in Example 14.

EXAMPLE 16

The tack temperature measured as above for the compositions of Examples 3, 4, 5, 7, 11, 14 and 15 are set forth in Table II:

TABLE VII

| Composition | % XAMA 2 (w/w) | Tack temperature |
| --- | --- | --- |
| Example 3 | 0 | 31 |
| Example 3 | 0.32 | 29 |
| Example 4 | 0.3 | 31 |
| Example 5 | 0.22 | 29 |
| Example 7 | 0 | 33 |
| Example 7 | 0.30 | 33 |
| Example 11 | 0.25 | 27 |
| Example 14 | — | 33 |
| Example 15 | 0.25 | 29 |

EXAMPLE 17

A warm-activated pressure-sensitive adhesive assembly was prepared as follows. A solution containing (a) 26 parts by weight of polymer comprising 84% hexadecylacrylate, 13% hexyl acrylate and 3% acrylic acid, and exhibiting a weight average molecular weight (in toluene) of $1.2 \times 10^6$ (b) 66.6 parts by weight heptane, and (c) 7.4 parts by weight methyl ethyl ketone, was used to cast a film on a release liner backing of siliconized polypropylene paper. A #90 wire-wound coating rod (Paul N. Gardner Co.) was used such that the final wet coating was approximately 1.75 mils thick. After air drying, the film thickness was approximately 10 mils. The film was heated in an incubator (convection) oven for 18 hours at 50° C. The final dried adhesive film was approximately 2.5 mils thick and exhibited a melting temperature of 29° C.

The film assembly or the transfer device produced above was used to apply the hot melt film in the first of two operations. First, the device was placed with the adhesive face down on Whatman paper stock #4. The assembly was heated to about 35° C. and rolled with a standard 4.5 lb roller. The adhesive film had formed a strong bond with, and had indeed transferred to the paper during this process, as evidenced by the fact that the release liner could be separated from the adhesive film but the adhesive film was now inseparable from the paper.

Designs were drawn on the adhesive-backed paper while it was being conditioned at room temperature (approximately 25° C.). The release liner was then removed. The adhesive coating appeared to be smooth and tack-free. Small shapes were cut from this paper and positioned on the edges of another sheet of white bond paper to enhance its appearance.

The following step constitutes the second phase of the experiment. The cut-out designs could be repositioned easily because there was no tackiness at all. When the arrangement was satisfactory, it was covered by a thin piece of cardboard and placed between two steel plates. The assembly was then placed in an oven maintained at 35° C. for five minutes. The steel plate acted as a gentle press. The assembly was then disassembled and the white bond paper with its designs were immediately examined in a room-temperature (approximately 24° C.) environment.

It was apparent that the designs were permanently affixed to the bond paper. Even when the paper was placed in the refrigerator, the designs remained in place and were stable.

EXAMPLE 18

A "chill-off" label was prepared as follows. A solution containing (a) 25 parts by weight of a 40:60 mixture of polymers, the first polymer comprising 84% hexadecylacrylate, 13% hexylacrylate and 3% acrylic acid and exhibiting a weight average molecular weight (in tetrahydrofuran) of $1.9 \times 10^6$, the second polymer comprising 74% hexadecylacrylate, 20% isodecylacrylate and 6% acrylic acid and exhibiting a weight average molecular weight (in toluene) of 50,000, and (b) containing 75 parts by weight of solvent composed of a 90:10 mixture of hexane:methylethylketone, was used to cast a film on a release liner backing of siliconized polypropylene paper. An appropriate wire-wound coating rod was used such that a final wet coating was approximately 1.25 mils thick. After air drying, the film was approximately 1.25 mils thick. The adhesive assembly resembled a normal PSA article. The film assembly was heated in an incubator (convection) oven for 18 hours at 50° C. The final dried adhesive film was 1.25 mils thick and exhibited a melting temperature of 21° C. The coating process and drying process was repeated to produce a final dried adhesive film thickness of 2.5 mils.

The transfer device produced above was placed with the adhesive face down on Whatman paper stock #4. The assembly was heated to about 40° C. and rolled with a standard 4.5 lb roller to cause the adhesive polymer to flow into the interstices of the cellulosic fibers of the paper. The adhesive film had formed a strong bond with, and had indeed transferred to, the paper during this process, as suggested by the fact that the release liner could be separated from the adhesive film, but the adhesive film was now inseparable from the paper.

The assembly was cut into strips about ⅜" wide and 2" long. These strips and the substrates to which they were applied after removal of the release liner were conditioned at ambient temperature (approximately 24° C.). The selected substrates were test tubes, synthetic leather, plastic and metal pens, painted-wood pencils and a small varnished article of wood.

The strips bonded well to each of the substrates. Attempts to remove them resulted in tearing of the paper label. This result demonstrates and substantiates the tamper-proof feature of this assembly.

When the label-bonded substrates were placed in a cold chest maintained at 5° C. for 15 minutes, the labels were easily removed without tearing the paper. The adhesive did not transfer to the substrate leaving the surface free of any marring.

EXAMPLE 19

A polymer was prepared by heating twenty seven grams of ethyl triglycol methacrylate, (Rohmtek TM), seventy five grams of octadecylmethacrylate and five grams of acrylic acid in 200 ml of ethyl acetate containing 0.4 g of AIBN initiator, at 65° C. for 10 hours. The resultant polymer had a DSC melting point of 35° C. A forty percent solids content solution of the polymer in a mixture of heptane and methyl ethyl ketone, in the ratio of 90/10, was cast on a Hytrel TM backing using a Meyer TM rod to give a 1 mil coating after drying at 90° C. for 30 minutes. The adhesive coated Hytrel TM had a MVTR of 484 g/m²/24 hours at 37° C. and a humidity difference of 100% to 10%, using the procedure of ASTM E 96–90. The adhesive was not tacky at room temperature.

The polymer solution was also coated onto siliconized Mylar TM and transfer coated onto a Celgard TM, (Hoechst Celanese), porous polyethylene film. The film was peel tested on a stainless steel substrate at 30° C. and gave 145 g/cm. When applied to the fore arm of human volunteers for one hour, the 180° peel test using an Instron TM at 10 inches per minute, was 95 g/inch at ambient skin temperature, and 40 g/inch when the adhesive film was cooled with an ice cube for 10 seconds. This showed a reduction in peel strength of 57%.

EXAMPLE 20

Twenty grams of ethoxy ethyl acrylate, eighty grams of hexadecyl acrylate, three point five grams of acrylic acid, 0.5 grams of AIBN and 200 mils of ethyl acetate were heated under nitrogen at 50° C. for 24 hours. After precipitating into ethanol, the mixture was dissolved into heptane at 30% solids and a 1 mil coating cast onto a Hytrel TM backing. The MVTR was 511 g/m²/24 hours when tested at 37° C. and a relative humidity difference of 100% to 10%, when tested according to the procedure of ASTM E 96–90.

When measured on the fore arm of human volunteers, the 180° peel strength was 125 g/cm at ambient skin temperature and 45 g/cm when cooled with ice for 10 seconds, this being a reduction in peel strength on cooling of 64%.

The instant invention has been shown and described herein in what is considered to be the most practical, and preferred embodiments. It is recognized, however, that departures may be made therefrom which are within the scope of the invention, and that modifications will occur to one skilled in the art upon reading this disclosure.

I claim:

1. A temperature-sensitive adhesive assembly which comprises
  (1) a body member:
  (2) secured to the body member, a layer of a polymeric composition which
    (a) comprises 40 to 100% by weight of at least one crystalline polymer which (i) begins to melt at a temperature $T_0$, where $T_0$ is 5° to 50° C., (ii) completes melting at a peak melting temperature $T_m$ which is at most $(T_0+15)$° C., and (iii) is a side-chain crystallizable polymer which has a heat of fusion of at least 20 Joules/g and contains at least 50% by weight of repeating units of the formula

wherein
    M is an atom forming part of the backbone of the polymer
    S is a spacer unit, and
    C is a crystallizable group,
    (b) has an ASTM D2979 tack value of less than 25 g.cm/sec at a temperature below $T_0$, and
    (c) has an ASTM D2979 tack value of at least about 100 g.cm/sec over a range of temperatures above $T_m$;
said assembly having one or more of the following characteristics I to VI:
  I. the layer of polymeric composition has a thickness of at least 0.001 inch:
  II. the crystalline polymer contains units derived from at least two monomers;
  III. the crystalline polymer has been crosslinked:
  IV. the polymeric composition comprises at least two polymers;

V. the body member is a woven fabric, a non-woven fabric, paper, wood, metal, glass, a medical immobilization device, an electrode, a surgical dressing, or a transdermal drug delivery patch; and VI. the assembly further comprises
(3) a release layer which covers the surface of the polymeric composition remote from the body member.

2. An assembly according to claim 1 wherein said repeating units are derived from at least one n-alkyl acrylate or methacrylate in which the alkyl group contains 14 to 22 carbon atoms.

3. An assembly according to claim 1 wherein the polymer contains 1 to 10% by weight of units derived from acrylic acid.

4. An assembly according to claim 1 wherein the polymer includes repeating units derived from the group consisting of acrylic acid, hydroxyethylacrylate, acrylamide, methacrylamide, methacrylic acid, linear or branched alkyl acrylates and methacrylates in which the alkyl group is not crystallizable, styrene and substituted styrenes.

5. An assembly according to claim 1 wherein the side-chain crystallizable polymer contains units derived from at least one polar monomer selected from polyoxalkylenes, acrylates, acrylamides, and methacrylamides.

6. An assembly according to claim 1 wherein the layer of polymeric composition has a thickness of at least 0.001 inch.

7. An assembly according to claim 1 wherein the crystalline polymer has been crosslinked.

8. An assembly according to claim 1 wherein the polymeric, composition comprises at least two polymers.

9. An assembly according to claim 1 wherein the body member is a woven fabric, a non-woven fabric, paper, wood, metal, glass, a medical immobilization device, an electrode, a surgical dressing, or a transdermal drug delivery patch.

10. An assembly according to claim 1 further comprising a release layer which covers the surface of the polymeric composition remote from the body member.

11. An assembly according to claim 1 wherein the body member is a polymeric film.

12. An assembly according to claim 1 wherein the polymeric composition has an ASTM D2979 tack value of less than 25 g.cm/sec at 25° C.

13. An assembly according to claim 1 wherein $T_0$ is 20°–35° C.

14. An assembly according to claim 1 wherein $T_0$ is 25°–30° C.

15. An assembly according to claim 1 wherein $T_m$ is at most $(T_0+10)°$ C.

16. An assembly according to claim 1 wherein $T_m$ is at most $(T_0+5)°$ C.

17. An assembly according to claim 1 wherein the polymeric composition has a crystallization temperature of 15° to 25° C.

18. An assembly according to claim 1 wherein the crystalline polymer has been crosslinked.

19. An assembly according to claim 1 wherein the polymeric composition also contains a conventional pressure-sensitive adhesive.

20. An assembly according to claim 1 wherein the body member is a flexible backing.

21. An assembly according to claim 1 which is a surgical drape.

22. An assembly according to claim 1 which is a label.

23. An assembly according to claim 1 wherein the layer of polymeric composition is substantially non-tacky at temperatures below $T_0$ and rapidly becomes tacky when heated to a temperature of $T_m$.

24. An assembly according to claim 1 which is substantially non-tacky at room temperature and rapidly becomes tacky when pressed against human skin.

25. A temperature-sensitive adhesive assembly which comprises
(1) a body member;
(2) secured to the body member, a layer of a polymeric composition which
(a) comprises 40 to 100% by weight of at least one crystalline polymer which (i) begins to melt at a temperature $T_0$, where $T_0$ is 5° to 50° C., (ii) completes melting at a peak melting temperature $T_m$ which is at most $(T_0+15)°$ C., and (iii) is polytetrahydrofuran,
(b) has an ASTM D2979 tack value of less than 25 g.cm/sec at a temperature below $T_0$, and
(c) has an ASTM D2979 tack value of at least about 100 g.cm/sec over a range of temperatures above $T_m$.

26. An assembly according to claim 25 wherein the layer of polymeric composition is substantially non-tacky at temperatures below $T_0$ and rapidly becomes tacky when heated to a temperature of $T_m$.

27. An assembly according to claim 25 which is substantially non-tacky at room temperature and rapidly becomes tacky when pressed against human skin.

28. An assembly according to claim 25 wherein the layer of polymeric composition has a thickness of at least 0.001 inch.

29. An assembly according to claim 25 wherein the body member is a woven fabric, a non-woven fabric, paper, wood, metal, glass, a medical immobilization device, an electrode, a surgical dressing, or a transdermal drug delivery patch.

* * * * *